(12) United States Patent
Venables et al.

(10) Patent No.: US 9,308,048 B2
(45) Date of Patent: Apr. 12, 2016

(54) PUNCTURE INDICATING GLOVES

(75) Inventors: Helena Venables, Wirral (GB); Simon Pickard, Cheshire (GB); Gareth Hilton, Wigan (GB); James Doran, Wigan (GB)

(73) Assignee: Regent Medical Limited (GB)

( * ) Notice: Subject to any disclaimer, the term of this patent is extended or adjusted under 35 U.S.C. 154(b) by 782 days.

(21) Appl. No.: 13/378,370

(22) PCT Filed: Jun. 22, 2010

(86) PCT No.: PCT/GB2010/051031
§ 371 (c)(1),
(2), (4) Date: Dec. 15, 2011

(87) PCT Pub. No.: WO2011/001164
PCT Pub. Date: Jan. 6, 2011

(65) Prior Publication Data
US 2012/0090074 A1 Apr. 19, 2012

(30) Foreign Application Priority Data
Jul. 2, 2009 (GB) .................................. 0911531.2

(51) Int. Cl.
*B32B 27/08* (2006.01)
*A61B 19/04* (2006.01)
*B32B 1/08* (2006.01)

(52) U.S. Cl.
CPC ...................................... *A61B 19/04* (2013.01)

(58) Field of Classification Search
CPC ... A61B 19/04; Y10T 428/1352; B32B 27/08
USPC ..................... 428/34.1, 34.2, 35.7, 35.9, 36.9
See application file for complete search history.

(56) References Cited

U.S. PATENT DOCUMENTS

| 5,224,221 | A | 7/1993 | Richardson |
| 2006/0070167 | A1 | 4/2006 | Eng et al. |
| 2006/0141186 | A1 | 6/2006 | Janssen et al. |
| 2006/0210737 | A1* | 9/2006 | Wang et al. ................... 428/35.2 |
| 2008/0279905 | A1* | 11/2008 | Kawamoto et al. ........... 424/402 |
| 2009/0070918 | A1 | 3/2009 | Pickard et al. |

FOREIGN PATENT DOCUMENTS

| EP | 0815880 | | 1/1998 |
| EP | 1360940 | | 11/2003 |
| GB | 2433227 | A  * | 6/2007 |
| GB | 2453000 | | 3/2009 |
| WO | 9003632 | | 4/1990 |
| WO | 9920203 | | 4/1999 |

OTHER PUBLICATIONS

International Search Report and Written Opinion dated Oct. 12, 2010 in Application No. PCT/GB2010/051031.
Search Report dated Oct. 21, 2009 in priority Application No. GB0911531.2.

* cited by examiner

*Primary Examiner* — Marc A Patterson
(74) *Attorney, Agent, or Firm* — Kilpatrick Townsend & Stockton LLP

(57) ABSTRACT

A surgical glove has inner and outer surfaces. At least one of the surfaces is treated with a treatment consisting of a non-ionic hydrocarbon solution with a carbon chain in the range of 8-16 and containing a hydrophilic functionality with a pH within the range 4.5-6.5. After treatment, the treated surface or surfaces are dried, the glove packaged and then irradiated. The treatment controls the initial contact angle of the surface to be less than 70 degrees, so that liquid material will spread quickly across the treated surface or surfaces, thereby ensuring that the presence of the liquid, indicative of the glove having been compromised, is visible to the wearer or other observer as quickly as possible.

46 Claims, No Drawings

PUNCTURE INDICATING GLOVES

CROSS REFERENCE TO RELATED APPLICATIONS

This application is the U.S. national phase of International Application No. PCT/GB2010/051031 filed on Jun. 22, 2010, and published in English on Jan. 6, 2011, as International Publication No. WO 2011/001164 A1, which application claims priority to Great Britain Patent Application No. 0911531.2 filed on Jul. 2, 2009, the contents of both of which are incorporated herein by reference.

The present invention relates to gloves, in particular surgical gloves which have puncture evident characteristics by means of which a wearer can easily identify if the glove has been pierced.

Surgical gloves perform an important function of protecting the wearer's hands from exposure to bodily fluids such as blood which might be infected and hence present a health risk as well as protecting the patient's internal organs from exposure to sweat and the like from the surgeons hands. Accordingly, the integrity of the liquid barrier formed by the glove is very important. In practice, surgical gloves are used within an environment where there is a risk of piercing, for example from scalpels and other sharp surgical implements, and it is therefore desirable for the wearer to be able to easily identify if a glove has been pierced, either before or during use, so as to minimize any potential contamination either to the wearer or the patient.

U.S. Pat. No. 5,224,221 describes a tamper or damage evident surgical glove in the form of a bi-layer glove, comprising an inner layer and an outer layer, in which the outer layer is translucent, in particular yellow, and the inner layer is a contrasting colour, in particular a darker colour such as green or black. If either the inner or outer layer is pierced, liquid can permeate between the two layers. This liquid causes two effects; the colour of the inner layer becomes more apparent through the outer layer, and or the colour of the liquid becomes apparent through the outer layer. The user sees this as a region of contrasting colour where the liquid is present between the two layers of the bilayer. However, the change in visibility produced by the indicating system in U.S. Pat. No. 5,224,221 has been found, in practice to be dependent on circumstance and in certain cases not to be that easily perceived by the wearer.

To maximize the perception of loss of barrier properties it is preferred that there is a large difference in colour or shade between regions of the bilayer that have fluid present between the two layers and regions of the bilayer that are absent of fluid, as discussed in British patent applications nos. GB 0801602.4 and GB 078240.5 and in U.S. patent application Ser. No. 12/170,453. Large differences or contrast in colour result in an obvious indication of loss of barrier properties to the user. This is much preferred over a bilayer that results in a small difference in colour that is much less obvious to the user. As the user is reliant on a colour change to indicate the bilayer has been compromised it is imperative that the colour change is obvious. The present invention seeks to provide a bilayer system of the type of U.S. Pat. No. 5,224,221 that results in a large region of strong colour as fluid ingresses into the region between the bilayers. In particular, the present invention seeks to maximize the conspicuity of the coloured region that becomes apparent in a double glove system by specifying the opacity of the outer glove the density and strength of colour of the under glove, and the surface properties of inner and outer glove.

The fluids generally exposed to the indicating system in the field of the invention are generally aqueous in nature but they are not of consistent colour. The colour of the fluid can range from colourless, transparent fluid such as water to strongly coloured fluid such as blood. As the fluid provides the source for indication of loss of barrier properties it is preferred to have a coloured under glove that contrasts with indicating fluid such as blood. It is also preferred that the colour of the under glove is strong enough to show through a transparent over glove when the indicating fluid is colourless and transparent.

Furthermore, in practice it is not only the strength of colour that is important to providing a early indication of loss of barrier properties. Strength of colour of the indicated region is important to ensure that puncture is obvious to the user. However, it is also important that the indicating region becomes apparent relatively quickly. The principle of a gloving system that can provide puncture indication is that the user is alerted to the potential loss of barrier properties and once aware of a potential problem can take action to ensure that a new barrier is put in place. In a surgical situation this is achieved by replacing one or more pairs of gloves. Therefore it is imperative that the initial indication of loss of barrier properties is relatively rapid. This allows the user to change their glove relatively rapidly and minimize the potential exposure to contaminated fluid. The longer it takes for users to identify puncture the greater the risk of cross contamination and hence potential transfer of infectious material between patient and user. Therefore it is much preferred that the coloured region on loss of barrier properties becomes visible relatively quickly.

The present invention is based partly on the realization that the surface properties of both gloves and the transparency of the over glove are important to generating optimal indication. The user relies on a colour change visible from the exterior of the glove on ingress of indicating fluid to indicate that the barrier properties of the bilayer have been compromised. The colour change occurs due to an increase in the amount of colour from the under glove or the indicating fluid showing through the outer glove. The intensity of colour of the inner glove does not change but the fluid ingressing into the space between the gloves results in the inner glove becoming more visible through the outer glove.

However, to ensure that loss of barrier properties is detected relatively rapidly the gloves need to have optical properties to ensure that the fluid containing region is conspicuous against the region that is absent of fluid. Even so, if the fluid remains in a relatively small locus around the point of breach a relatively small region of indication will result. Even if the contrast in colour is strong, it may still be difficult to see due to the size of the region. Therefore to ensure that the indicated region is visible quickly it is equally if not more important that the indicating region is relatively large.

Large wetted areas arise quickly, which are advantageous to early detection by the wearer, if fluid spreads rapidly between the surfaces of the glove. This is effectively achieved if the surface properties of the under glove and over glove have an affinity for the ingress liquid.

As the fluids that come into contact with gloves in a surgical environment are aqueous, the speed of propagation of the indicating region is governed by the contact angle of inner surface of the outer glove and the contact angle of the outer glove, which controls the speed the aqueous liquid moves between the two gloves.

According to a first aspect of the present invention there is provided a surgical glove having an inner surface and an outer surface, one of said inner and outer surfaces having an initial contact angle of less than 70 degrees.

A glove in accordance with the invention has the advantage that aqueous material will spread across the surface of the sufficient quickly to effectively identify to the user that the integrity of the glove has been compromised in an acceptable time period. The glove is, therefore, particularly effective for use as either an inner or outer glove part of a bilayer glove, depending on which surface has the contact angle within the requirements of the invention. The contact angle of the surface of the respective glove which faces towards the abutting surface of the other glove ensures rapid spreading of aqueous material which leaks between the inner and out glove, either due to compromise of the inner glove or the outer glove.

According to a second aspect of the present invention there is provided a puncture indicating glove comprising a bilayer formed by an under glove layer and an outer glove layer, the under glove layer having an outer surface which faces an inner surface of the outer glove layer, at least one of said inner and outer surfaces having a contact angle in accordance with the invention.

Preferably both the outer surface of the inner glove and the inner surface of the outer glove have a contact angle in accordance with the invention.

The contact angle parameter relates to the speed at which a drop of liquid spreads over the surface. When the drop first touches the surface, it will, of course, be a point contact and therefore have a contact angle of 180 degrees (for at least an instant the spherical drop will sit on the surface as a complete sphere).

As the drop spreads, the contact area between the drop and the surface increases as a circular chordal surface. The contact angle is then defined geometrically as the angle formed by a liquid at the three phase boundary where a liquid, gas and solid intersect, Conventionally, as the case in this patent application, the angle is measure through the liquid phase rather than the gas phase. Therefore a contact angle of 180° describes wetting in which liquid does not wet the surface and 0° describes the situation where the liquid wets very well to the point at which it is difficult o define the droplet on the surface as it lies totally flat. Since the initial contact is a point contact at the bottom of the drop, the initial angle is always 180 degrees, regardless of the properties of the material on which it is dropped. When the drop forms a perfect hemisphere at the surface, the angle will have decreased to 90 degrees. If the surface is has a strong affinity for the liquid surface, the drop will eventually be completely absorbed and hence have a contact angle of 0 degrees. Contact angle is often dynamic with time, especially when surfaces have an affinity for the liquid. The speed at which the contact angle decreases is important to the invention.

The reference above and hereinafter to the initial contact angle is to be understood to be the contact angle of the liquid drop on the surface within 0.5 seconds, which parameter will clearly vary depending on the material.

Preferably, said one of said inner and outer surfaces of the glove has an initial contact angle of less than 50 degrees. More particularly, said surface has a contact angle of less than 40 degrees within 10 seconds, preferably within 5 seconds. More especially, a contact angle of less than 30 degrees within 10 seconds, preferably within 5 seconds. Still further a contact angle of less than 20 degrees within 10 seconds, preferably within 5 seconds, and of particular advantage is a contact angle of less than 10 degrees within 10 seconds.

In the present invention, contact angles were determined by adding drops of pure water to the surface of gloves using the following methods The dynamic drop behaviour was measured using the movie function on a contact angle measuring instrument such as a Data physics OCA 20 or a Kruss Easy drop DSA 20. A 9 microliter drop was allowed to just release from the syringe and fall from the minimum height onto the surface. Recording was started just before the drop released. Up to 25 images a second were recorded for varying lengths of time depending how soon the drop became more static, up to a maximum of 1 minute. The contact angles, (both sides of the drop) were measured retrospectively on each frame by the instrument.

The surface properties of the gloves can be controlled to vary the contact angle using a number of methods well known to the skilled person in the art. Chlorination is the preferred method for ensuring that the wetting properties are optimal. However, a number of other methods can also be used to optimize the wetting properties of the gloves which include the addition of hydrophilic coatings or the addition of surfactants.

In particularly preferred embodiment, the contact angle is controlled by coating the gloves with a treatment consisting of a hydrocarbon solution with a carbon chain within the range of 8-16 and containing a hydrophilic functionality with a pH within the range of 4.5-6.5. After treatment, the gloves are then packaged and irradiated.

The treatment may be applied in a number of different ways. In one embodiment, the treatment is applied in a concentrated form to the gloves and then dried. In another embodiment, the treatment is applied as a solution to the gloves at a concentration of less than 10% via a washing mechanism known in the art, after which the gloves are again dried prior to packaging and irradiating.

In yet another embodiment, the treatment is agitated to produce a foam before applying the foam to the gloves. The gloves are then dried prior to packaging and irradiating. A still further embodiment has the treatment sprayed into a vessel containing the gloves and mixed thoroughly prior to drying, packaging and irradiation.

The hydrocarbon solution used in the invention are non-ionic, in order to achieve a low irritancy potential. Examples of suitable treatments are Sorbitan Laurate, Alkyl(8-16)polyglucoside, Capryl/capramidopropyl betaine, Sodium Lauryl Sulfoacetate, Cocamidopropyl betaine, glyceryl laurate, Sucrose stearate, and Sucrose distearate. Mixtures of these have also been found to work.

Preferably, the glove according to the invention has a chroma range C* (which essentially is the strength of colour) which is controlled to result in a glove that indicates optimally with transparent liquid and strongly coloured liquids such as blood. This makes the glove particularly useful as an inner or under-glove in a bi- or multi-layer glove system when used in conjunction with an outer glove whose opacity changes with to make the visibility of the inner glove increase when aqueous material ingresses between the layers. In that case, the contrasting colour of the inner layer makes it more visible to the wearer when compromise has occurred.

The chroma of the glove is preferably greater than 30, advantageously greater than 40, more preferably greater than 43, more especially greater than 46 and in particular greater than 50. The chroma is preferably controlled by the inclusion of pigment and can be increased by choosing pigments of relatively high values of C* as well as increasing the levels of said pigment. This ensures that the maximum colour difference is observed on wetting with transparent fluid such as water or when the indicating fluid is more highly coloured as in the case when blood is the indicating medium. If the chroma of the glove is relatively small (weakly coloured) the indicator system will not work well with fluids of low chroma (e.g. water).

As already discussed above, whilst the contact angle of the relevant surface of the glove is important to ensure rapid spreading of the aqueous material, if the presence of that material cannot easily be discerned due to, for example, only a small colour change, it will still be difficult for the wearer to notice that integrity of the barrier has been compromised. To put it another way, if the indicating region is not conspicuous due to poor colour contrast, the large size of the indicating will not matter as it will always be difficult to see. Therefore it is still important that the colour of the indicating region contrasts with the colour of the double layer that is absent of fluid. Large, highly contrasting regions result in faster indication.

The level of contrast or difference in colour between the bilayer containing fluid and the bilayer absent of fluid is partially determined by the transparency or opacity of the outer glove. The opacity of the outer glove can be determined using a method similar to that described in ISO 2814. If the outer glove is truly transparent (that is having an opacity of 0%) the colour of the underglove will always be visible through the outer glove. If this is the case ingress of a colourless fluid will have little impact on the colour of the double layer when viewed from the outside, being visible essentially only at the edge of the liquid. This results in little colour change on indication and little perception of puncture to the user. If the overglove is of low translucency (that is having an opacity of 100%) the over glove will mask the under glove. Therefore the apparent colour to the user will be of the overglove. When liquid ingresses into the space between the two layers the over glove will continue to mask the colour of the under glove and any colour associated with the fluid. Therefore there will be little change of colour on indication. Both these systems will result in a low probability that the user will detect the occurrence of a puncture in the barrier.

According to a third aspect of the present invention there is provided a puncture indicating glove comprising a bilayer formed by an inner glove layer and an outer glove layer, the outer glove having an opacity in the range of 10-40%.

A puncture indicating glove in accordance with this aspect of the invention has the advantage that it provides particularly effective indication of liquid penetration between the layers, making it particularly easy for the wearer to identify if the integrity of the barrier formed by the glove has been compromised.

The opacity range referred to above and hereinafter is based on a range of 0%, being completely transparent, to 100% being totally opaque. Preferably, the opacity is in the range of 15 to 40%, advantageously 23 to 40% and more particularly 20 to 35%. This has the advantage that it results in the largest contrast in colour when transparent liquids ingress between the layers.

The opacity of the over glove is preferably controlled by the inclusion of a fine particulate material such as, but not limited to: titanium dioxide, silica, barite powder, barium sulphate, barium carbonate, calcium carbonate, gypsum, clay, talc, alumina white, basic magnesium carbonate, zinc oxide etc in the over glove. The levels of materials required to achieve the desired opacity will depend on the nature of the material and particle size of the particulate material along with the amount of particulate material contained in the compounding formulation for the polymer. For this reason it is preferred to minimize the amount and size of particulate material used in the formulation of the polymer constituents to make up the glove.

Preferably, the second and third aspects of the invention as defined above are combined so that at least one of the faces surfaces of the inner and outer gloves has a contact angle in accordance with the requirements set out above.

The inner or under glove preferably has a chroma range $C^*$ (which essentially is the strength of colour) which is controlled to result in a glove that indicates optimally with transparent liquid and strongly coloured liquids such as blood. The chroma of the inner glove is preferably greater than 30, advantageously greater than 40, more preferably greater than 43, more especially greater than 46 and in particular greater than 50. The chroma is preferably controlled by the inclusion of pigment and can be increased by choosing pigments of relatively high values of $C^*$ as well as increasing the levels of said pigment. This ensures that the maximum colour difference is observed on wetting with transparent fluid such as water or when the indicating fluid is more highly coloured as in the case when blood is the indicating medium. If the chroma of the underglove is relatively small (weakly coloured) the indicator system will not work well with fluids of low chroma (e.g. water).

The depth of density of colour is not solely controlled by $C^*$ as black or dark grey undergloves would have a relatively low $C^*$ but appear to provide good contrast on the ingress of liquid. Therefore it is preferred that if $C^*$ is low $L^*$ [0.1] should be relatively low, and in particular that $L^*$ is less than than 45, preferably less than 35 and more preferably less than 32 $L^*$ is a measure of the lightness of the colour and varies from 0 for black to 100 for white.

Furthermore, to encompass both the properties of $C^*$ and $L^*$ it is advantageous that the product of $C^*$ and $1/L^*$ is greater than 0.6, more preferably greater than 0.8 and in particular greater than 1.

Preferably the inner glove is of a colour having a hue angle in the range of 160-300°, advantageously 180-280°, more preferably 220-270° and in particular 250-270°). This has the advantage that it results in a glove in which the inner glove contrasts well with blood, so that in the case of the indicating medium being blood, the inner layer may be visible through the fluid that ingresses to give indication on puncture. To give the greatest perception of colour change it is preferred that the under glove has a colour that contrasts with red. This will also ensure that indication becomes apparent when examining the gloves in an environment that is predominantly red in colour.

In an advantageous development of the puncture indicating glove of the invention, a middle layer is disposed between the inner and outer layers, which middle layer has a refractive index which varies depending on its liquid content—in particular, the opacity of the material of the middle layer decreases, so that it becomes more transparent, in the presence of liquid, thereby increasing the visibility of the inner layer when liquid is present. It is, then, highly preferably that both the inner surface of the outer layer and the outer surface of the inner layer have a contact angle in accordance with the first aspect of the invention so as to ensure rapid spreading of moisture whether it be the outer surface or the inner surface that is compromised.

It is, then, of still further advantage for both surfaces of the middle layer to have contact angles meeting the values and ranges specified above so as to maximize the effectiveness of the indication system.

The degree of colour change can be measured by determining the value of $\Delta E^*$ (Euclidean distance) on the ingress of fluid between the layers—the larger the value of $\Delta E^*$ the greater the colour change. This leads to and increased probability of perception of failure of barrier properties. With regards to this $C^*$, $L^*$, $a^*$, $b^*$ (The three basic coordinates represent the lightness of the color (L*, L*=0 yields black and L*=100 indicates white), its position between red/magenta and green (a*, negative values indicate green while positive values indicate magenta) and its position between yellow and blue (b*, negative values indicate blue and positive values indicate yellow), and ΔE* values (all of which are universally recognized parameters with regard to colour within the art—CIE 1976 commission Interntionale de l'Eclairage) may be determined using a spectrophotometer such as an SP62 provided by X-Rite of Grandville Mich. This method can also be used to determine the preferred properties of the underglove. The colour characterization of gloves can be performed using either CIELAB system or a CIELCH system.

$$\Delta E^* = ((L^*_{standard} - L^*_{sample})^2 + (a^*_{standard} - a^*_{sample})^2 + (b^*_{standard} - b^*_{sample})^2)^{0.5}$$

$$C^* = (a^{*2} + b^{*2})^{0.5}$$

$$h^\circ = \arctan(b^*/a^*)$$

When performing these measurements it is important to ensure the background is consistent, as the colour of the background may affect the colour of the glove under evaluation. Measurements for this document were all performed by placing a single layer of material over either a ceramic plate or a ceramic former used for glove manufacture with L* of 81.95 to 90.69, an a* of −0.87 to 0.13 and a b* of 2.79 to 11.82. The colour of the underglove was measured on the former or plate. An overglove was placed over the underglove and the colour measured of the composite. Liquid was then injected into the gap between the underglove and the over glove and the colour determined of the composite in a region containing the liquid. It is important that sufficient liquid is injected into the gap to give a large area in which the colour of the underglove becomes more apparent through the overglove. For this purpose 0.5-1.0 ml of liquid was injected into the gap between the two glove layers. Both distilled water and synthetic blood were used as the liquid. The values for ΔE* were then determined on indication using the equation above. Where L*, a* and b* for the standard refer to the values determined for the combination of the gloves with no liquid present and L*, a* and b* for the sample all refer to those measured for areas of the bilayer after injection of liquid.

Synthetic blood was used to meet the specification described in ASTMF 1862-00a. For this purpose synthetic blood meeting this specification was purchased from Johnson, Moen & Co., 2505 Northridge Lane NE, Rochester, Minn. 55906.

The colour and wetting properties of the underglove alone can be used to achieve an optimal underglove that can be used universally with a number of over gloves. Although it is preferred that these properties in combination with the opacity and wetting properties of the outer glove define the properties of an indicating system comprising of an inner glove an outer glove to give advantageous results in terms of recognition of ingress of liquid between the layer of the glove.

The following are examples of contact angles achieved using the present invention. Protegrity SMT gloves are included here by way of example of poor contact angle on natural rubber gloves, comparable to prior art synthetic gloves with no treatment at all.

| | Contact angle (°) | |
|---|---|---|
| Product | Initial (t = 5 seconds) | Final (t = 20 seconds) |
| Protegrity SMT | 84.18 | 72.84 |
| Biogel Polyisoprene Indicator Underglove | 83.25 | 79.7 |
| Biogel Poly Isoprene Indicator Underglove with treatment | 30.45 | 11.7 |
| Biogel Skinsense Indicator Underglove (Polychloroprene) | 79.7 | 78.6 |
| Biogel Skinsense Indicator Underglove (Polychloroprene) with treatment | 9.7 | 4.6 |

Examples of contact angles on Biogel Polyisoprene Indicator Underglove with chosen treatment pre and post irradiation

| Pre-irradiation | | Post irradiation | |
|---|---|---|---|
| Initial (t = 5 seconds) | Final (t = 20 seconds) | Initial (t = 5 seconds) | Final (t = 20 seconds) |
| 3.46° | 0° | 2.15° | 0.5° |

The invention claimed is:

1. A surgical glove having an inner surface and an outer surface, one of said inner and outer surfaces treated to provide a rapid spreading of aqueous material upon contact, such that a drop of aqueous material on the treated surface of the surgical glove has a contact angle on the treated surface of less than 70 degrees within 0.5 seconds and a contact angle of less than 40 degrees within 10 seconds.

2. The glove according to claim 1, wherein the inner surface of the glove has the contact angle of less than 70 degrees within 0.5 seconds and less than 40 degrees within 10 seconds, the glove being formed of a material having a chroma C* which is greater than 30.

3. The glove according to claim 2, wherein the chroma is greater than 40.

4. The glove according to claim 1, wherein the outer surface of the glove has the contact angle of less than 70 degrees within 0.5 seconds and less than 40 degrees within 10 seconds, the glove being formed of a material having an opacity in the range of 10-40%.

5. A puncture indicating glove comprising a bilayer formed by an under glove layer and an outer glove layer, the under glove layer having an outer surface which faces an inner surface of the outer glove layer, at least one of the inner surface of the outer glove and the outer surface of the under glove treated to provide a rapid spreading of aqueous material upon contact, such that a drop of aqueous material on either the inner surface or the outer surface has a contact angle of less than 70 degrees within 0.5 seconds.

6. The glove according to claim 5, wherein both the outer surface of the under glove layer and the inner surface of the outer glove layer have the contact angle of less than 70 degrees within 0.5 seconds.

7. The glove according to claim 5, wherein a middle layer is disposed between said under and outer glove layers, the middle layer being formed of a material whose refractive index varies depending on its liquid content so that the opacity of the middle layer decreases in the presence of liquid.

8. The glove according to claim 7, wherein the middle layer has an inner surface and an outer surface, at least one of the inner surface or the outer surface of the middle layer having a contact angle with a drop of aqueous material that is less than 70 degrees within 0.5 seconds.

9. The glove according to claim 5, wherein the under glove layer is formed of a material having a chroma C* which is greater than 30.

10. The glove according to claim 9, wherein the chroma is greater than 40.

11. The glove according to claim 5, wherein the outer glove layer is formed of a material having an opacity in the range of 10-40%.

12. The glove according to claim 4, wherein the opacity is in the range of 15 to 40%.

13. The glove according to claim 1, wherein each surface whose contact angle is less than 70 degrees within 0.5 seconds and less than 40 degrees within 10 seconds has a treatment applied thereto consisting of a hydrocarbon solution with a carbon chain within the range of 8-16 and containing a hydrophilic functionality, the solution comprising a pH within the range of 4.5-6.5.

14. The glove according to claim 13, wherein the glove is irradiated.

15. The glove according to claim 13, wherein the hydrocarbon solution is non-ionic.

16. The glove according to claim 13, wherein the hydrocarbon solution includes at least one of Sorbitan Laurate, Alkyl(8-16)polyglucoside, Capryl/capramidopropyl betaine, Sodium Lauryl Sulfoacetate, Cocamidopropyl betaine, glyceryl laurate, Sucrose stearate, and Sucrose distearate, or mixtures thereof.

17. The glove according to claim 1, formed of synthetic material.

18. A method of controlling the contact angle of at least one surface of the surgical glove according to claim 5, comprising treating at least one of the inner surface and the outer surface with a treatment consisting of a hydrocarbon solution with a carbon chain within the range of 8-16 and containing a hydrophilic functionality, the solution comprising with a pH within the range of 4.5-6.5.

19. The method according to claim 18, wherein said hydrocarbon solution is non-ionic.

20. The method according to claim 18, comprising the further step of irradiating each treated surface after treatment.

21. The method according to claim 20, wherein irradiating is carried out after the glove has been packaged.

22. The method according to claim 18, wherein the treatment is applied in a concentrated form to each said surface of the gloves and then dried.

23. The method according to claim 18, wherein the treatment is applied as a solution to each said surface of the glove at a concentration of less than 10%.

24. The method according to claim 23, wherein the solution is applied via a washing mechanism.

25. The method according to claim 18, wherein the treatment is agitated to produce a foam before applying the foam to each surface of the glove.

26. The method according to claim 18, wherein the treatment is sprayed into a vessel containing the glove and mixed thoroughly, after which the glove is dried.

27. The method according to claim 18, wherein the hydrocarbon solution is non-ionic.

28. The method according to claim 18, wherein the hydrocarbon solution includes at least one of Sorbitan Laurate, Alkyl(8-16)polyglucoside, Capryl/capramidopropyl betaine, Sodium Lauryl Sulfoacetate, Cocamidopropyl betaine, glyceryl laurate, Sucrose stearate, and Sucrose distearate, or mixtures thereof.

29. The method according to claim 18, wherein the contact angle of each said surface is less than 50 degrees within 0.5 seconds.

30. The method according to claim 18, wherein each said surface has a contact angle of less than 30 degrees within 10 seconds.

31. The method according to claim 18, wherein each said surface has a contact angle of less than 20 degrees within 10 seconds.

32. The method according to claim 18, wherein each said surface has a contact angle of less than 10 degrees within 10 seconds.

33. The glove according to claim 1, wherein the treated surface has a contact angle of less than 30 degrees within 10 seconds.

34. The glove according to claim 1, wherein the treated surface has a contact angle of less than 20 degrees within 10 seconds.

35. The glove according to claim 1, wherein the treated surface has a contact angle of less than 10 degrees within 10 seconds.

36. The glove according to claim 3, wherein the chroma is greater than 43.

37. The glove according to claim 3, wherein the chroma is greater than 46.

38. The glove according to claim 3, wherein the chroma is greater than 50.

39. The glove according to claim 9, wherein the chroma is greater than 43.

40. The glove according to claim 9, wherein the chroma is greater than 46.

41. The glove according to claim 9, wherein the chroma is greater than 50.

42. The glove according to claim 1, wherein the treated surface has a contact angle of less than 40 degrees within 5 seconds.

43. The glove according to claim 4, wherein the opacity is in the range of 20 to 35%.

44. The glove according to claim 17, wherein the synthetic material comprises polychloroprene or polyisoprene.

45. The glove according to claim 5, wherein a drop of aqueous material has a contact angle of less than 40 degrees within 10 seconds.

46. A surgical glove having an inner surface and an outer surface, one of said inner and outer surfaces treated to provide a rapid spreading of aqueous material upon contact, such that a drop of aqueous material on the treated surface of the surgical glove has a contact angle on the treated surface of less than 50 degrees within 0.5 seconds.

* * * * *